United States Patent
Wu et al.

(10) Patent No.: US 9,109,212 B2
(45) Date of Patent: Aug. 18, 2015

(54) **METHOD FOR ENHANCING EXTRACELLULAR SECRETION OF RECOMBINANT PROTEINS IN *ESCHERICHIA COLI* BY CO-EXPRESSING *THERMOBIFIDA FUSCA* CUTINASE**

(71) Applicant: Jiangnan University, Wuxi (CN)

(72) Inventors: Jing Wu, Wuxi (CN); Lingqia Su, Wuxi (CN); Jian Chen, Wuxi (CN)

(73) Assignee: Jiangnan University, Wuxi, JS (CN)

( * ) Notice: Subject to any disclaimer, the term of this patent is extended or adjusted under 35 U.S.C. 154(b) by 0 days.

(21) Appl. No.: 13/935,519

(22) Filed: Jul. 4, 2013

(65) Prior Publication Data

US 2014/0011239 A1 Jan. 9, 2014

(30) Foreign Application Priority Data

Jul. 5, 2012 (CN) .......................... 2012 1 0241426
Sep. 3, 2012 (CN) .......................... 2012 1 0338830

(51) Int. Cl.
| | |
|---|---|
| *C12N 15/00* | (2006.01) |
| *C12N 9/18* | (2006.01) |
| *C12N 9/20* | (2006.01) |
| *C12P 21/00* | (2006.01) |
| *C12P 21/02* | (2006.01) |
| *C12N 9/26* | (2006.01) |
| *C12N 9/24* | (2006.01) |
| *C12N 9/42* | (2006.01) |

(52) U.S. Cl.
CPC ................ *C12N 9/20* (2013.01); *C12N 9/2408* (2013.01); *C12N 9/248* (2013.01); *C12N 9/2414* (2013.01); *C12N 9/2434* (2013.01); *C12P 21/00* (2013.01); *C12P 21/02* (2013.01)

(58) Field of Classification Search
CPC ................................ C12N 15/00; C12P 21/00
USPC .................................... 435/69.1, 320.1, 252.3
See application file for complete search history.

(56) References Cited

U.S. PATENT DOCUMENTS

| | | | | |
|---|---|---|---|---|
| 5,429,950 | A * | 7/1995 | Power et al. ................... | 435/198 |
| 5,512,203 | A * | 4/1996 | Kolattukudy et al. ......... | 510/392 |
| 6,207,436 | B1 * | 3/2001 | Bjornvad et al. .............. | 435/209 |
| 6,815,190 | B1 * | 11/2004 | Abo et al. ...................... | 435/198 |
| 6,995,005 | B1 * | 2/2006 | Deckwer et al. .............. | 435/196 |
| 8,445,250 | B2 * | 5/2013 | Isaksen et al. ................ | 435/195 |
| 8,679,826 | B2 * | 3/2014 | Yamamoto et al. ........... | 435/278 |

(Continued)

OTHER PUBLICATIONS

Su et al, Microbial Cell Factories, Jan. 12, 2012, vol. 11, pp. 1-7, Extracellular overexpression of recombinant *Thermobifida fusca* cutinase by alpha-hemolysin secretion system in *E. coli* BL21 (DE3).*

(Continued)

*Primary Examiner* — Albert Navarro
*Assistant Examiner* — Ginny Portner
(74) *Attorney, Agent, or Firm* — Lili Chen (57) ABSTRACT

The present invention provides a method of increasing extracellular secretion of secretory proteins by co-expressing the secretory proteins with a mature cutinase. Cutinase can improve the permeability of *E. coli* cell membrane without destroying the membrane, and thus facilitate cross-membrane transfer of the secretory proteins co-expressed in *E. coli*. Increased extracellular secretion of target proteins can shorten cell culture time, reduce the formation of inclusion bodies and increase production of target proteins.

5 Claims, 4 Drawing Sheets (56) References Cited

U.S. PATENT DOCUMENTS 8,785,169 B2* 7/2014 Chen et al. .................... 435/197
2003/0119054 A1* 6/2003 Mrksich et al. ................ 435/7.1
2012/0149086 A1* 6/2012 Chen et al. .................... 435/197

OTHER PUBLICATIONS

Chen, S et al, Indentification and Characterization of Bacterial Cutinase, J. Biological Chemistry, vol. 283, pp. 25854-25862, 2008.*
Su et al, Applied and Environmental Microbiology, Jul. 2013, published on-line Apr. 2013, vol. 79(14, pp. 4192-4198, Extracellular location of *Thermobifida fusca* cutinase Expressed in *Escherichia coli* BL21(DE3) without mediation of a signal peptide.*
Chen, S et al, Applied Biochemistry and Biotechnology, 2011, vol. 165, pp. 666-675, Study on Improvement of Extracellular Production of Recombinant *Thermobifida fusca* Cutinase by *Escherichia coli*.*
Ferreira, BS et al, Applied Microbiol. Biotechnol. 2003, vol. 61, pp. 69-76, Towards a cost effective strategy for cutinase production by a recombinant *Saccharomyces cerevisiae*: strain physiological aspects.*

* cited by examiner

METHOD FOR ENHANCING EXTRACELLULAR SECRETION OF RECOMBINANT PROTEINS IN *ESCHERICHIA COLI* BY CO-EXPRESSING *THERMOBIFIDA FUSCA* CUTINASE

CROSS-REFERENCES AND RELATED APPLICATIONS

This application claims the benefit of priority of Chinese patent application serial no. 201210241426.7, entitled "A method for extracellular expression of *Thermobifida fusca* cutinase", filed Jul. 5, 2012, and Chinese patent application serial no. 201210338830.6, entitled "A method for enhancing extracellular secretion of recombinant proteins and its application", filed Sep. 3, 2012, which are herein incorporated by reference in entirety.

BACKGROUND OF THE INVENTION

1. Field of the Invention

The present invention relates to a method for enhancing extracellular secretion of recombinant proteins, and more particularly relates to a method for enhancing extracellular secretion of recombinant proteins in *Escherichia coli* by co-expressing *Thermobifida fusca* (*T. fusca*) cutinase.

2. Description of the Related Art

*Escherichia coli* (*E. coli*) has a rapid growth rate and high protein expression level so that it has been considered as one of the most promising strain for industrial production of recombinant proteins. *E. coli* is able to express proteins in 3 ways: cytosolic production, periplasmic production and extracellular production. Compared with other two methods, extracellular production has significant advantages in both analytical and industrial applications because it does not require cell disruption and has almost no contamination from host proteins.

There are 5 secretory pathways for protein to translocate across the cell membrane in *E. coli*. However, due to their complicated components, regulatory mechanisms, and/or the low intrinsic secretion capabilities of these systems, *E. coli* is usually considered to be a poor secretor of proteins. It has been reported that the balance between expression level and secretion rate is a critical factor for extracellular production of recombinant proteins. To date, many strategies for improving the extracellular secretion of proteins in *E. coli* have been reported, especially the mechanism between transport chaperon protein and target proteins has been explored. Enhancing protein secretion process, constructing outer membrane leakage mutations as well as adding certain chemicals to enhance the permeability of cell membrane are commonly used methods.

Cutinase not only catalyzes the cleavage of the ester bonds of cutins, but also is capable of hydrolyzing soluble esters, insoluble triglycerides and a variety of polyesters. In addition to its hydrolytic activity, cutinase is also used in ester synthesis and transesterification. As a multifunctional enzyme, cutinase has potential in the food, chemical, textile, and other industries. Enzymes with cutinase activity have been found in both fungi and bacteria. To date, all the cutinase from microorganisms have been found to be secretory enzymes. Therefore, for the heterologous expression, signal peptides are usually used to mediate the secretion of recombinant cutinase. Using this approach, *Fusarium solani* cutinase has been expressed in a variety of host cells. The highest yield of extracellular protein 546 mg/L, was obtained in a 5 L bioreactor using an engineered *Saccharomyces cerevisiae* cellular system. Previously, we identified the open reading frame responsible for the expression of *T. fusca* cutinase, and secretory expression of the cutinase was performed by mediation of the pelB signal peptide in *E. coli* BL21 (DE3). More recently, we found that the mature form of *T. fusca* cutinase without a signal peptide was mainly secreted into the culture medium and only a small percentage of the enzyme is located in the periplasm and cytoplasm. We further found that the mature cutinase has phospholipase activity that leads to limited hydrolysis of phospholipids of cell membrane and thus increases membrane permeability. Based on this finding, the present invention provides a method for extracellular secretion of mature cutinase without mediation of a signal peptide and a method for enhancing extracellular secretion of recombinant proteins. Mature cutinase used herein refers to a full-length cutinase protein without a signal peptide.

DETAILED DESCRIPTION

The present invention provides a method for extracellular secretory expression of *Thermobifida fusca* cutinase (*T. fusca* cutinase, NCBI accession number AAZ54921) in *E. coli* without mediation of a signal peptide and a method for enhancing extracellular secretion of recombinant proteins in *E. coli* by co-expressing mature *T. fusca* cutinase. The methods mainly comprise plasmid construction without any signal peptide, expressing *T. fusca* cutinase and co-expressing target proteins with *T. fusca* cutinase.

The method for secretory expression of *T. fusca* cutinase in *E. coli* without mediation of a signal peptide comprises the following steps:

1. Plasmid Construction

The mature cutinase gene without the signal peptide sequence (124-906 bp in the gene sequence of NCBI accession number AAZ54921) was amplified from Tfu_0883/pET-20b(+) (Sheng Chen, Xing Tong, Ronald W. Woodard, Guocheng Du, Jing Wu and Jian Chen. Identification and Characterization of Bacterial Cutinase. Journal of Biological Chemistry. 2008. 283(38): 25854-62.) by a polymerase chain reaction. The PCR product was isolated, amplified and ligated into the expression vector pET-20b(+). The resulting recombinant plasmid Tfu_0883/pET-20b(+)$^{NS}$, which has a full-length *T. fusca* cutinase gene without any signal peptide, was verified by DNA sequencing.

2. Expression of Recombinant Cutinase

The recombinant plasmid Tfu_0883/pET-20b(+)NS was transformed into *E. coli*, and the transformed *E. coli* cells were cultivated and induced to express cutinase. The culture broth was centrifuged and the supernatant was collected for purification of cutinase.

The *E. coli* host strain could be any of *E. coli* BL21 (DE3), *E. coli* W3110, *E. coli* JM109, *E. coli* JM109 (DE3) and *E. coli* DH5α, among which the *E. coli* BL21 (DE3) was preferred.

The vector used for protein expression could be any of pUC, pET, pT7-7, and pGEX.

The method for enhancing extracellular secretion of recombinant proteins by co-expressing *T. fusca* cutinase comprises the following steps:

1. Plasmid Construction

The Tfu_0883/pETDuet-1 and the recombinant plasmid pET-20b (+) containing a gene encoding a target protein were excised using two restriction enzymes. And the target protein gene was ligated into Tfu_0883/pETDuet-1 to make a Tfu_0883/target protein/pETDuet-1 plasmid. The Tfu_0883/target protein/pETDuet-1 plasmid, which contains genes for mature *T. fusca* cutinase and the target protein, was amplified in *E. coli* JM109.

2. Expression of Target Protein

The Tfu_0883/target protein/pETDuet-1 plasmid containing genes encoding *T. fusca* cutinase and the target protein was transformed into *E. coli* and the transformed *E. coli* was cultivated for target protein expression. After that, the culture broth was centrifuged and the supernatant was collected for target protein purification.

The host strain for expression could be any of *E. coli* BL21 (DE3), *E. coli* W3110, *E. coli* JM109, *E. coli* JM109 (DE3) and *E. coli* DH5α, among which the *E. coli* BL21 (DE3) was preferred.

The vector used for expression could be any of pETDuet-1, pCOLADuet-1, pUC, pET, pT7-7 and pEGX.

The target proteins are secretory proteins that are synthesized in the cytoplasm and, with the help of transport proteins, are transferred across inner and outer cell membrane, and secreted into the culture medium through a secretion pathway. The secretion pathway can be Type I, II, III, IV, and V secretory pathway in *E. coli* cells. The Type II secretion pathway mediated by SecB is preferred. The target proteins can be, for example, intrinsic *E. coli* secretory proteins or proteins with an *E. coli* signal peptide for extracellular secretion.

The method of constructing Tfu_0883/pETDuet-1 that contains cutinase gene from *T. fusca* was described in Chinese patent application no. 201210045965.3, which is herein incorporated by reference in its entirety.

The present invention uses mature cutinase to significantly improve the permeability of *E. coli* cell membrane and enhance the extracellular secretion of recombinant proteins without destroying the cell membrane, which can significantly decrease formation of inclusion bodies, shorten cell culture time, and increase productivity. This method has important applications in large scale production of industrial proteins.

EXAMPLES

The following examples were provided by way of illustration only, and not by way of limitation. Standard experimental operations not specifically described in the specification were preformed according to standard molecular cloning protocols described in "Molecular Cloning: A Laboratory Manual" (by Sambrook J and Russell D, Cold Spring Harbor Laboratory Press, 2001).

Strains, Vectors and Materials:

*Streptomyces* sp. FA1 and *Bacillus licheniformis* were from China Center for Type Culture Collection (CCTCC), and the CCTCC accession numbers were M 2012310 and M 2013012, respectively. The strain *T. fusca* (ATCC 27730) was obtained from ATCC. *E. coli* JM109 strain was used as the host for gene cloning and *E. coli* BL21 (DE3) strain was used for protein expression.

The plasmid Tfu_0883/pET-20b (+) (Sheng Chen, Xing Tong, Ronald W. Woodard, Guocheng Du, Jing Wu and Jian Chen. Identification and Characterization of Bacterial Cutinase. Journal of Biological Chemistry. 2008. 283(38): 25854-62.) harboring the gene of *T. fusca* cutinase (NCBI accession number AAZ54921) and purified wild-type cutinase from the culture medium of *T. fusca* were laboratory stock. The pET-20 b (+) and pETDuet-1 vector from Novagen (a company of EMD Chemicals, Philadelphia, Pa., USA) were utilized as expression vectors.

The restriction enzymes, alkaline phosphatase, T4 DNA ligase, agarose gel DNA purification kit and pMD18-T simple vector were obtained from TakaRa (Dalian, China). The DNA sequencing and primer synthesis were performed by Shanghai Sangon Biological Engineering Technology & Services Co., Ltd (Shanghai, China). The 4-Nitrophenyl butyrate (pNPB) was obtained from Sigma (Shanghai, China). Other chemicals were obtained from Sinopharm Chemical Reagent Co., Ltd (Shanghai, China).

Example 1

Construction of Tfu_0883/pET-20b(+)$^{NS}$ Plasmid

Construction of Tfu_0883/pET-20b(+)$^{NS}$ plasmid comprised the following steps:

(1) The gene encoding a mature cutinase (124-906 bp in the gene sequence of NCBI accession number AAZ54921) was amplified from Tfu_0883/pET-20b (+), which contained the full length cutinase gene of NCBI accession number AAZ54921 inserted in Nco I and EcoR I restriction enzyme sites of plasmid pET-20b), by polymerase chain reaction using the primers P1 (SEQ ID No: 1) and P2 (SEQ ID No: 2) in 50 μL PCR system. SEQ ID No. 1: gTAATC CATATggCCAACCCCTACgAgCgC (With restriction enzyme Nde I cutting site). SEQ ID No. 2: AgA gAATTCgggAACgggCAggTggAgCg (With restriction enzyme EcoR I cutting site). The PCR process was as follows: denaturation at 94° C. for 4 min, cyclical reaction for 30 times (98° C. for 10 s, 60° C. for 5 s, 72° C. for 1 min), elongation at 72° C. for 10 min, and finally being kept at 4° C. After gel purification, the PCR products were ligated into pMD18-T Simple vector and then transformed into *E. coli* JM109. The transformation products were spread on LB agar plate containing ampicllin (LB-Amp) for overnight cultivation at 37° C. The single colony was transferred into liquid LB for plasmid amplification. The recombinant plasmid was then verified by DNA sequencing.

(2) A plasmid with the correct sequence of the *T. fusca* cutinase gene and vector pET-20b(+) were separately digested with the restriction enzymes, Nde I (Nde I has a restriction enzyme cutting site located upstream of intrinsic pelB signal peptide) and EcoR I. To get the recombinant plasmid Tfu_0883/pET-20b (+)$^{NS}$, the gel band purification products were then ligated by T4 DNA ligase at 16° C. for overnight. And then, the recombinant plasmids were transformed into *E. coli* JM109. The transformation products were spread on LB-Amp agar plate for overnight cultivation at 37° C. The single colony was transferred into liquid LB-Amp for plasmid amplification. 8-10 h later, plasmids Tfu_0883/pET-20b (+)$^{NS}$ were extracted, purified and verified by DNA sequencing.

Example 2

Expression of Tfu_0883/pET-20b(+)$^{NS}$ by *E. coli* BL21 (DE3)

Expression of Tfu_0883/pET-20b(+)$^{NS}$ by *E. coli* BL21 (DE3) comprised the following steps:

After transformation, *E. coli* BL21 (DE3) containing Tfu_0883/pET-20b (+)$^{NS}$ was cultivated on LB-Amp agar plate for overnight at 37° C. The single colonies were transferred into liquid LB-Amp and cultivated to later logarithmic phase. The culture broth was inoculated into liquid TB (Containing 100 µg/mL Amp) with 5% inoculation percent and grown at 37° C. for 2 h. Lactose was added to a final concentration of 5 g/L and the temperature was lowered to 25° C. for induction.

Figure 1:
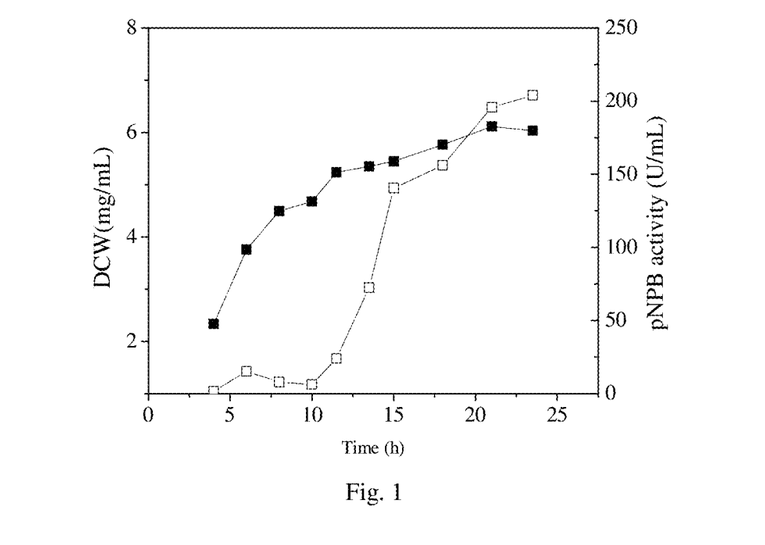
FIG. 1. Time profiles for the production of cutinase by *E. coli* BL21 (DE3)/Tfu_0883/pET-20b $(+)^{NS}$ in a shaking flask. ■, Dry cell weight (DCW); □, cutinase activity in the culture supernatant.
Figure 2:
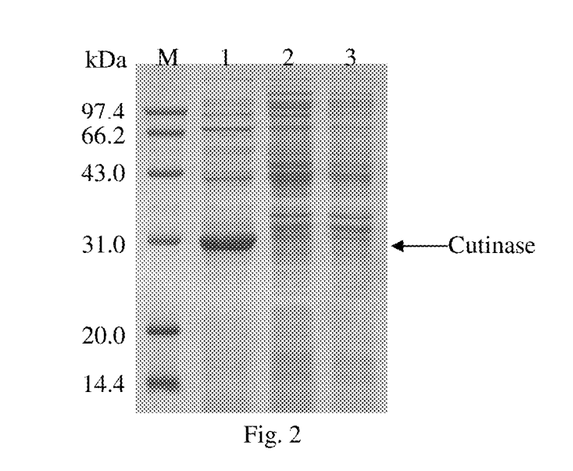
FIG. 2. SDS-PAGE analysis of the expression of cutinase by *E. coli* BL21 (DE3)/Tfu_0883/pET-20b $(+)^{NS}$. M, molecular mass standard protein; 1, culture supernatant; 2, intracellular soluble fraction; 3, intracellular insoluble fraction.

As shown in FIG. 1, during cultivation in the shake flask, the cutinase activity in the culture medium increased rapidly from 12 h of post induction and reached a maximum of 204.8 U/mL at 24 h. However, the cutinase activity in the cytoplasm was only 10.1 U/mL at the same time, which meant the cutinase without a signal peptide was almost completely "secreted" into the medium. The distribution of the cutinase was investigated by SDS-PAGE. As shown in FIG. 2, one major band around 31 kDa which is in agreement with the calculated molecular weight of mature cutinase, was found in the culture medium. In addition, no visible band was observed in either the cytoplasm or the periplasm.

Example 3

3 L Bioreactor for Production of Cutinase

The extracellular "secretion" efficiency of the above *E. coli* BL21 (DE3) harboring cutinase was further explored in 3 L fermentor. Exponential fed-batch culture strategy at a controlled speed was carried out to produce cutinase using recombinant *E. coli* BL21 (DE3) high cell-density culture.

The 3 L bioreactor for production of cutinase comprised the following steps:

(1) During fermentation, when the initial carbon resource (Glycerol) worked out at 6 h, the fresh substrate was fed. The feed was exponentially increased and coincided with specific growth rate (µ=0.25 h$^{-1}$).

(2) When the OD600 of culture broth reached 50, lactose was added for induction at a flow rate of 0.6 g/L/hr.

Figure 3:
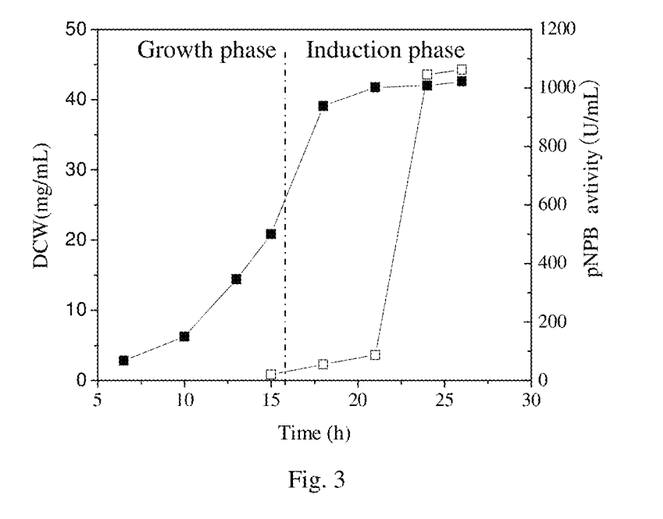
FIG. 3. Time profiles for the production of cutinase by *E. coli* BL21 (DE3)/Tfu_0883/pET-20 b $(+)^{NS}$ in a 3 L fermentor. ■, DCW; □, cutinase activity in the culture supernatant.

As shown in FIG. 3, the cutinase activity in the culture medium increased rapidly from 9 h of post induction and reached a maximum of 1063 U/mL that was 5.2 times higher than in the shake flask cultivation. In addition, the productivity 44.2 U/mL/h obtained by this way was 1.9 times than that obtained by utilizing secretory pathway Type I and represented the highest productivity reported to date. The excellent yield achieved in 3 L bioreactor by expressing *T. fusca* cutinase in *E. coli* without mediation of a signal peptide makes it possible that cutinase can be produced in industrial scale.

Example 4

Co-Express α-Amylase with *T. fusca* Cutinase

The method of co-expressing α-amylase with *T. fusca* cutinase comprises the following steps:

(1) Construction of recombinant plasmid Tfu_0883/amy/pETDuet-1. Plasmid Tfu_0883/pETDuet-1 containing gene encoding mature *T. fusca* cutinase inserted in Nco I and Hind III restriction enzyme sites of the first multiple cloning site of pETDuet-1, and plasmid amy/pET-20b (+) (Described in detail in Chinese patent application serial number: 201210274173.3) containing gene encoding α-amylase inserted in Nco I and Hind III restriction enzyme sites of pET-20b (+) were separately digested with the restriction enzymes, Nde I and Xho I. The gel band purification products were then ligated by T4 DNA ligase at 16° C. for overnight. And then, the recombinant plasmids were transformed into *E. coli* JM109. The transformation products were spread on LB (Containing 100 mg/L amp) agar plate for overnight cultivation at 37° C. The single colonies were transferred into liquid LB-Amp for plasmid amplification. The recombinant plasmid Tfu_0883/amy/pETDuet-1 containing genes of *T. fusca* cutinase and a-amylase inserted in the first and second multiple cloning site of pETDuet-1, respectively, was extracted, purified and verified by DNA sequencing.

(2) Expression of α-amylase. After transformation, *E. coli* BL21 (DE3) containing Tfu_0883/amy/pETDuet-1 were cultivated on LB-Amp agar plate at 37° C. for 8-10 hr. The single colonies were transferred into liquid LB-Amp and cultivated at 37° C. for 8-10 hr. The culture broth was inoculated into liquid TB (Containing 5 g/L glycerol, 12 g/L peptone, 24 g/L yeast extract, 12.54 g/L K$_2$HPO$_4$, 2.31 g/L KH$_2$PO$_4$ and 100 µg/mL Amp) with 5% inoculation percent and grown at 37° C. for 2 hr. Then, IPTG was added to the culture broth with a final concentration of 0.4 mM. The culture was continued for another 60 hr after induction at 30° C. The recombinant *E. coli* BL21 (DE3) harboring amy/pET-20b (+) expressing the individual target enzyme was cultured under the same conditions as control.

Figure 4:
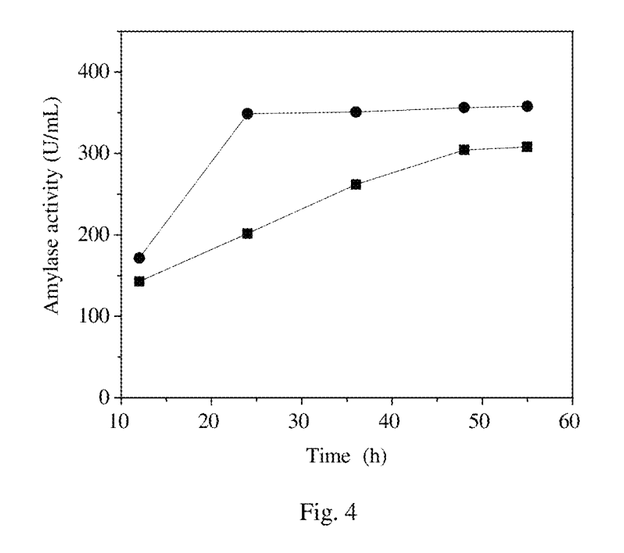
FIG. 4. Time profiles for the production of α-amylase by *E. coli* BL21 (DE3). ■, the recombinant *E. coli* BL21 (DE3) harboring amy/pET-20b(+) as control, ● *E. coli* BL21 (DE3) harboring Tfu_0883/amy/pETDuet-1.
Figure 5:
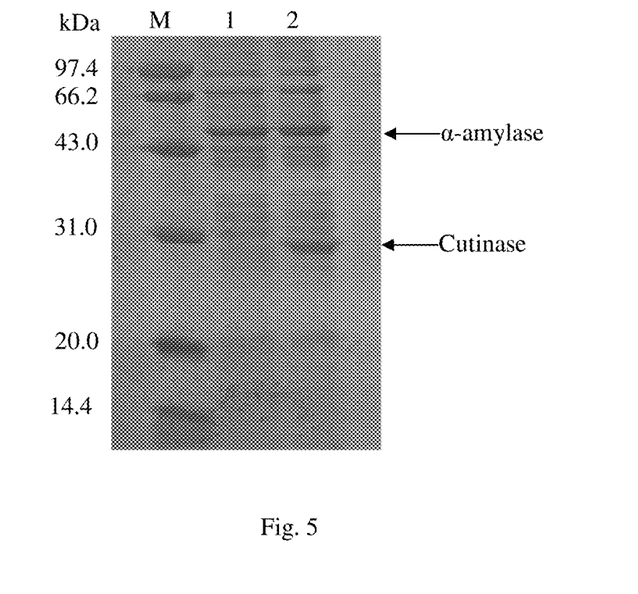
FIG. 5. SDS-PAGE analysis of the expression of α-amylase. M, molecular mass standard protein; 1, culture supernatant of *E. coli* BL21 (DE3) harboring amy/pET-20b(+); 2, culture supernatant of *E. coli* BL21 (DE3) harboring Tfu_0883/amy/pETDuet-1.

(3) Enzymatic activity assay. The supernatant which was derived from separating cells by centrifugation at 8000 rpm for 10 min at 4° C. was used to measure the α-amylase activity in the culture medium. As shown in FIG. 4, the maximum α-amylase activity in the culture medium was 308 U/mL when α-amylase was expressed alone, and 358 U/mL when α-amylase was co-expressed with cutinase. The yield of co-expression system was higher by 16.2%, but because of the shortened cultivation period by half, the productivity was improved significantly. In addition, no α-amylase activity was detected in the intracellular fragments at the end of the cultivation in either case, suggesting that α-amylase was totally secreted into the culture medium. SDS-PAGE analysis (FIG. 5) of the culture medium showed that one distinct band for α-amylase of similar molecular weight, about 53 kDa, was found in the culture medium in both cases.

Example 5

Co-Express Zylanase with T. fusca Cutinase

The method of co-expressing xylanase with T. fusca cutinase comprised the following steps:

(1) Construction of recombinant plasmid Tfu_0883/xynA/pETDuet-1. Plasmid Tfu_0883/pETDuet-1 containing gene encoding T. fusca cutinase and plasmid xynA/pET-20 b (+) (Described in detail in Chinese patent document, application number: 201210284346.X) containing gene encoding xylanase inserted in Nco I and EcoR I restriction enzyme sites of pET-20 b (+) were separately digested with the restriction enzymes, Nde I and Xho I. The gel band purification products were then ligated by T4 DNA ligase at 16° C. for overnight. And then, the recombinant plasmids were transformed into E. coli JM109. The transformation products were spread on LB (Containing 100 mg/L amp) agar plate for overnight cultivation at 37° C. The single colonies were transferred into liquid LB-Amp for plasmid amplification. plasmids The recombinant plasmid Tfu_0883/xynA/pETDuet-1 containing genes of T. fusca cutinase and xylanase inserted in the first and second multiple cloning site of pETDuet-1, respectively, were extracted, purified and verified by DNA sequencing.

(2) Expression of xylanase. After transformation, E. coli BL21 (DE3) containing Tfu_0883/xynA/pETDuet-1 was cultivated on LB-Amp (Containing 100 mg/L amp) agar plate at 37° C. for 8-10 h. The single colonies were transferred into liquid LB-Amp and cultivated at 37° C. for 8-10 h. The culture broth was inoculated into liquid TB (Containing 5 g/L glycerol, 12 g/L peptone, 24 g/L yeast extract, 12.54 g/L $K_2HPO_4$, 2.31 g/L $KH_2PO_4$ and 100 μg/mL Amp) with 5% inoculation percent and grown at 25° C. for 6 h. Then, IPTG was added to the culture broth with a final concentration of 0.1 mM. The culture was continued for another 60 h after induction. The recombinant E. coli BL21 (DE3) harboring xynA/pET-20b (+) expressing the individual target enzyme was cultured under the same conditions as control.

Figure 6:
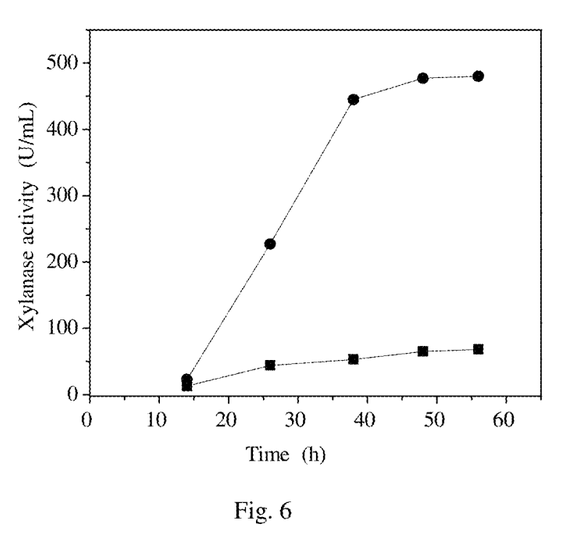
FIG. 6. Time profiles for the production of xylanase by *E. coli* BL21 (DE3). ■, *E. coli* BL21 (DE3) harboring xynA/pET-20b(+); ●, *E. coli* BL21 (DE3) harboring Tfu_0883/xynA/pETDuet-1.
Figure 7:
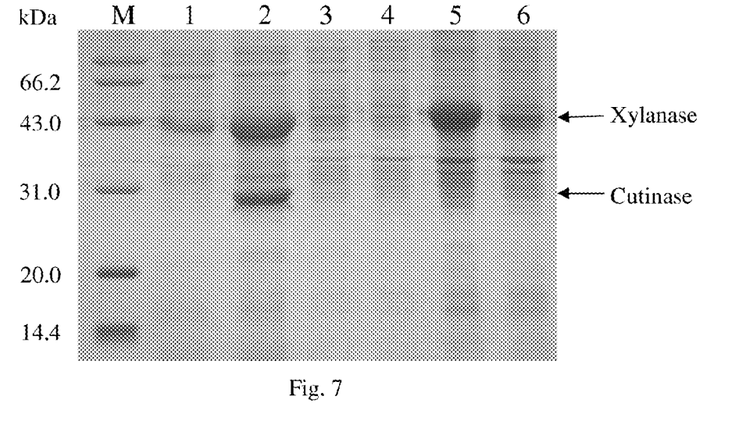
FIG. 7. SDS-PAGE analysis of the expression of xylanase. M, molecular mass standard protein; 1, extracellular fraction of *E. coli* BL21 (DE3) harboring xynA/pET-20b(+); 2, extracellular fraction of *E. coli* BL21 (DE3) harboring Tfu_0883/xynA/pETDuet-1; 3, intracellular soluble fraction of *E. coli* BL21 (DE3) harboring xynA/pET-20b(+); 4, intracellular soluble fraction of *E. coli* BL21 (DE3) harboring Tfu_0883/xynA/pETDuet-1; 5, intracellular insoluble fraction of *E. coli* BL21 (DE3) harboring xynA/pET-20b (+); 6, intracellular insoluble fraction of *E. coli* BL21 (DE3) harboring Tfu_0883/xynA/pETDuet-1.

(3) Enzymatic activity assay. The supernatant which was derived from separating cells by centrifugation at 8000 rpm for 10 min at 4° C. was used to measure the xylanase activity in the culture medium. As shown in FIG. 6, the maximum xylanase activity in the culture medium was 68 U/mL when xylanase was expressed alone, and 480 U/mL when xylanase was co-expressed with cutinase. The yield of co-expression system was higher by 6-fold, and the cultivation period was shortened by 10 h. In addition, at the end of the cultivation, the intracellular xylanase activity was 5.2 U/mL for the cells expressing xylanase alone and 8.8 U/mL for the co-expression system, suggesting that the majority of soluble xylanase had been secretes into the culture medium in both cases. Notably, SDS-PAGE analysis (FIG. 7) demonstrated the presence of inclusion bodies in the E. coli cells expressing xylanase alone, unlike that of the E. coli used in the co-expression system. The results presented here demonstrated that co-expressing cutinase accelerated the transport rate of target proteins, thus, the balance between expression level and secretion rate was achieved. Correspondingly, fewer inclusion bodies were observed by SDS-PAGE.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A method for secretory expression of T. fusca cutinase in E. coli without mediation of a signal peptide, comprising cloning a mature cutinase gene from T. fusca into an expression vector that does not comprise a signal peptide, expressing said mature cutinase in an E. coli host strain and obtaining said T. fusca cutinase from the culture supernatant.

2. The method of claim 1, comprising the steps of:
1) Amplify a gene encoding mature T. fusca cutinase from plasmid Tfu_0883/pET-20b(+) and ligate said T. fusca cutinase gene into vector pET-20b(+) to make a plasmid Tfu_0883/pET-20b(+)$^{NS}$, wherein the pelB signal peptide of pET-20b(+) plasmid is removed from said plasmid Tfu_0883/pET-20b(±)$^{NS}$;
2) Transform said plasmid Tfu_0883/pET-20b (+)$^{NS}$ into an *E. coli* host strain; and
3) Culture said *E. coli* harboring Tfu_0883/pET-20b(+)$^{NS}$, induce secretory expression of *T. fusca* cutinase, and obtain *T. fusca* cutinase from the culture supernatant.

3. The method of claim 1, wherein said *E. coli* host strain is selected from the group consisting of *E. coli* BL21 (DE3), *E. coli* W3110, *E. coli* JM109, *E. coli* JM109 (DE3) and *E. coli* DH5α.

4. The method of claim 2, wherein said *E. coli* host strain is selected from the group consisting of *E. coli* BL21 (DE3), *E. coli* W3110, *E. coli* JM109, *E. coli* JM109 (DE3) and *E. coli* DH5α.

5. The method of claim 1, wherein said host strain is *E. coli* BL21 (DE3).

* * * * *

SEQUENCE LISTING

```
<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: PCR Primer

<400> SEQUENCE: 1
gtaatccata tggccaaccc ctacgagcgc                                    30

<210> SEQ ID NO 2
<211> LENGTH: 29
<212> TYPE: DNA
<213> ORGANISM: Artificial Sequence
<220> FEATURE:
<223> OTHER INFORMATION: PCR Primer

<400> SEQUENCE: 2
agagaattcg ggaacgggca ggtggagcg                                     29
```